United States Patent [19]
Shaw, IV

[11] 3,980,073
[45] Sept. 14, 1976

[54] METHOD AND APPARATUS FOR AIDING DIAGNOSTIC SCANNING OF THE BODY OF A PATIENT

[75] Inventor: Alexander F. Shaw, IV, Davenport, Iowa

[73] Assignees: Neeley, Carletta M.; Carl R. Neeley, both of Spokane, Wash.

[22] Filed: Aug. 12, 1975

[21] Appl. No.: 604,021

Related U.S. Application Data

[62] Division of Ser. No. 551,264, Feb. 20, 1975.

[52] U.S. Cl. ............................ 128/2 H; 128/2.1 C; 128/21 Z; 73/344; 324/65 P
[51] Int. Cl.² .................... A61B 5/05; A61H 39/02
[58] Field of Search ................ 128/2 H, 2 R, 2.1 Z, 128/2.1 R, 2.1 C, 2.1 E; 73/344, 341, 342; 324/65 P

[56] References Cited
UNITED STATES PATENTS

| | | | |
|---|---|---|---|
| 2,012,112 | 8/1935 | States | 128/2 H |
| 2,328,853 | 9/1943 | Sherrard | 324/65 P |
| 3,064,641 | 11/1962 | Manenti | 128/2.1 R |
| 3,132,644 | 5/1964 | Smith | 128/2.1 R |
| 3,306,282 | 2/1967 | Pierce | 128/2 H |
| 3,491,595 | 1/1970 | Griffeth | 73/344 |
| 3,657,640 | 4/1972 | Jelinek et al. | 73/344 |
| 3,785,368 | 1/1974 | McCarthy et al. | 128/2.1 Z |

*Primary Examiner*—Robert W. Michell
*Assistant Examiner*—Lee S. Cohen
*Attorney, Agent, or Firm*—Henderson, Strom & Sturm

[57] ABSTRACT

A circuit having an amplifier coupled to an oscillator, the oscillator having a second amplifier and a feedback circuit. Changes in resistance between an electrode coupled to the circuit and a probe, also connected to the circuit, are responded to by the circuit. Output components are connected to the circuit for providing visual and audio signals corresponding to the resistance changes and for recording the changes upon a chart. The electrode is grasped by a patient, and the probe is the hand of a doctor using the technique of palpation upon the patient. The probe alternately is a structure, placed against the patient by the doctor, for simultaneously detecting the changes in resistance between the electrode and the structure and providing a second resistance change corresponding to the temperature of the portion of the patient contacted by the structure, the circuit responding to either resistance change to provide output signals corresponding to either the resistivity or the temperature of the contacted portion of the patient.

5 Claims, 4 Drawing Figures

U.S. Patent  Sept. 14, 1976  3,980,073
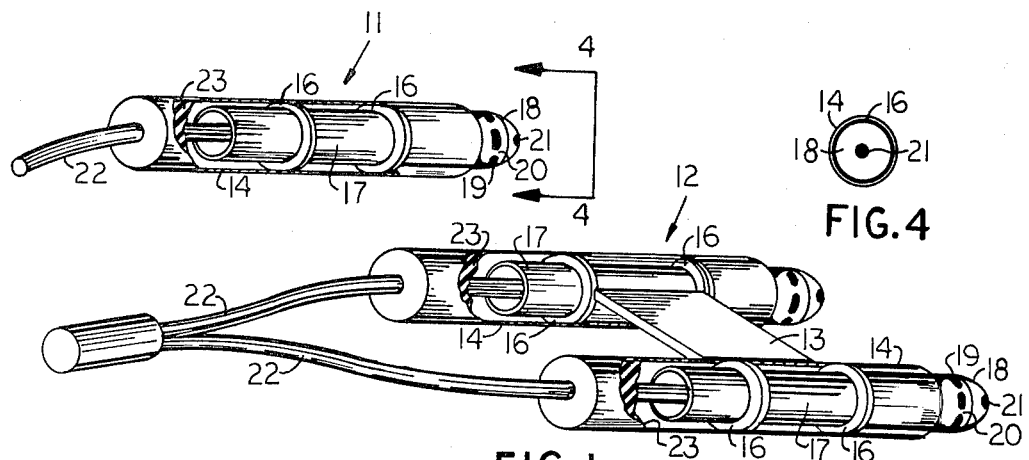
FIG. 4
FIG. 1
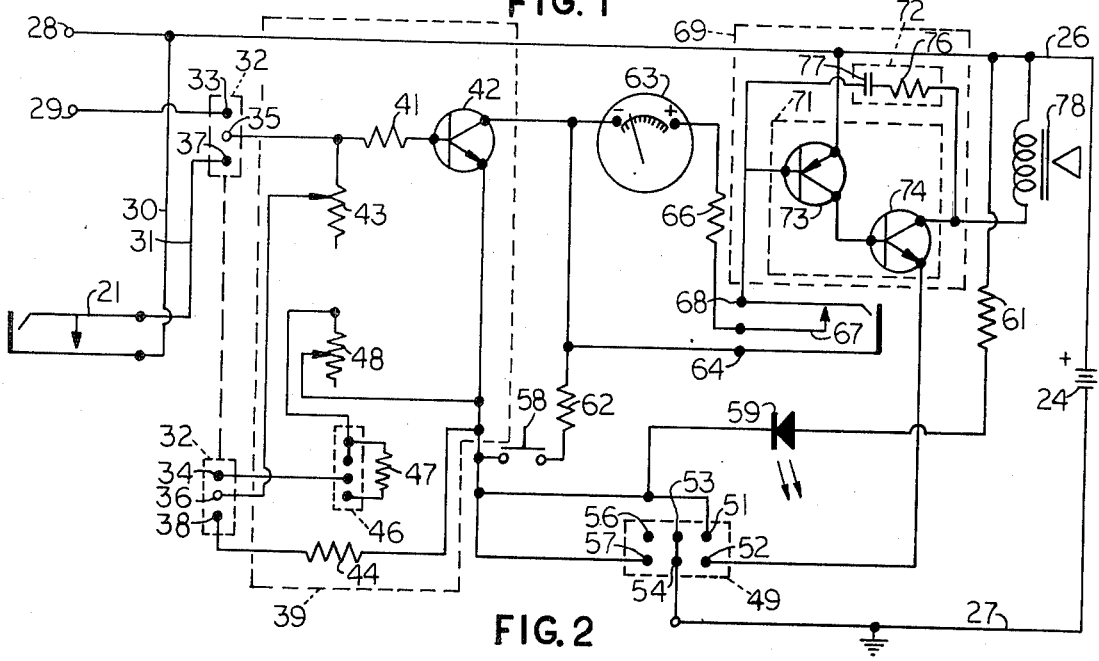
FIG. 2
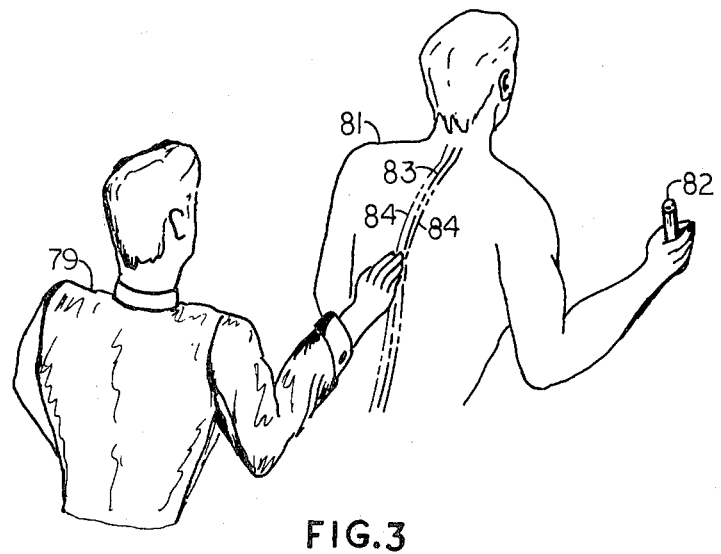
FIG. 3

METHOD AND APPARATUS FOR AIDING DIAGNOSTIC SCANNING OF THE BODY OF A PATIENT

This is a division of application Ser. No. 511,264, filed Feb. 20, 1975.

BACKGROUND OF THE INVENTION

This invention relates to medical diagnostic methods and apparatus. More particularly, it relates to those methods and apparatus which includes probes or electrodes which are placed against the body of the patient to be examined in order to detect temperature or resistance changes.

A number of devices are available which either detect the temperature of the body or of a particular organ of the body or detect the resistivity exhibited at points on the body surface or between two closely spaced points or the body surface, as in the galvanic skin response mechanisms common to lie detector apparatus. These devices are rather cumbersome and expensive. None of these devices combine temperature and resistivity measuring functions.

Areas of the body which exhibit increased conductivity and increased temperature include the acupuncture points of the body. Subluxations, situations of malpositioned contiguous vertebrae of the spine causing interference with the nerves and normal nervous transmission, trigger inflammation reactions of the body resulting in edema thereabout, which areas exhibit increased conductivity and increased temperature. Although the aforementioned apparatus may locate acupuncture points or areas along the spine which should be further examined for subluxations, precise location is difficult since either temperature or resistance measurements alone are relied upon.

SUMMARY OF THE INVENTION

According to this invention a method and apparatus are disclosed for aiding in the diagnostic scanning of the body of a patient. More particularly a method and apparatus for locating acupuncture points and areas of trauma along the spine of a patient are disclosed.

A probe is provided having external insulating and internal conducting members. The conducting member has a protruding tapered end with a temperature sensitive resistive member formed in the tip of the end. The tapered end conducts currents and heat from the body, and the resistive member responds to the heat to transmit a variable flow of current, the currents being used to detect resistance and temperarture changes of the area of the body against which the probe is pressed.

A potential difference is created between an electrode grasped by the patient and either a probe or an electrode grasped by the doctor. The other hand of the doctor or the probe is pressed against the back of the patient, thereby completing a circuit which includes a means responsive to changes in resistance and having an amplifier member and which includes a means for indicating the response having an oscillator member. The hand of the doctor or the probe is passed over the back of the patient and the resistances of the body areas are measured. The temperatures of the body areas are measured also when the probe is used. The circuit feeds back to the doctor the changes in resistance and temperature measured, whereby areas of the body of the patient to be closely examined and treated are more thoroughly located.

It is an object of this invention to provide a method and apparatus for aiding in medical diagnostic scanning of the body of a patient which method is novel and straightforward in practice and which apparatus is compact, economical to use and inexpensive to manufacture.

Another object of this invention is to provide a method and apparatus for more thoroughly locating points along the spine of a patient which should be more closely examined and treated.

Still another object of this invention is to provide a method and apparatus for more thoroughly locating acupuncture points upon the surface of the body of a patient.

Another object of this invention is to provide an apparatus which can be used for measuring galvanic skin response as part of a lie detector apparatus.

A further object of this invention is to provide a method and apparatus which method uses both temperature and resistance measurements to locate acupuncture points or points of medical interest along the spine of a patient and which apparatus simultaneously detects temperature and resistance changes.

These objects and other features and advantages of this invention will become readily apparent by reference to the following description when taken in conjunction with the accompanying drawings.

BRIEF DESCRIPTION OF THE DRAWINGS

The appended drawings illustrate the invention, wherein:

FIG. 1 is an isometric view of the single and double probes of this invention, portions of the probes being cut away to show internal structure;

FIG. 2 is a schematic diagram of the circuit of this invention;

FIG. 3 is a diagrammatic representation of a doctor practicing this invention upon a patient; and FIG. 4 is an end elevational view taken along line 4—4 of FIG. 1 and depicting the sensing tip of the single probe of this invention.

DESCRIPTION OF THE PREFERRED EMBODIMENT

Referring now to the drawings, a single probe structure of this invention is indicated generally at 11 in FIG. 1, and the dual probe structure is indicated generally at 12 in FIG. 1. The dual probe 12 includes two single probes 11 which are interconnected by a cross member 13; therefore, only a single probe 11 will be described hereinbelow.

The single probe 11, FIGS. 1 and 4, includes an external cylindrical member 14 made of an insulating material. Annular shaped insulating mountings 16 are uniformly spaced and affixed to the interior wall of the member 14. An internal cylindrical member 17, made of a conducting material, is mounted within the insulating mountings 16 and has a tapered end 18 which protrudes from the external cylindrical 14. Apertures 19 are formed about the periphery of the cylinder 17 adjacent to the tapered end 18, the end 18 being conducted to the rest of the cylinder 17 by a plurality of narrow portions 20. A thermistor 21, having a thermister bead with a glass coating and two lead wires (not shown), is affixed to the cylinder 17 at the tip of the tapered end 18. One lead (not shown) of the thermistor is attached to the cylinder 17, and the other lead (not shown) of the thermistor 21 passes through the lead 22 together with a lead (not shown) from the cylinder 17. Insulating material 23 is packed between the lead 22 and the external cylinder 14.

Referring to FIG. 2, the circuit of this invention includes a battery 24 connected between a first conductor 26 and a grounded second conductor 27. First and second inputs 28,29 are provided for resistivity measurement, and third and fourth inputs 30,31 are provided for temperature measurement.

A double pole double throw switch 32 has left and right upper contacts 33,34, center contacts 35,36 and lower contacts 37,38. The first and third inputs 28,30 are connected to the first conductor 26; the second input is connected to the left upper contact 33 of the switch 32; and the fourth input 31 is connected to the left lower contact 37 of the switch 32.

The switch 32 is connected to the first amplifier 39, the left center contact 35 being connected through a resistor 41 to the base of the NPN transistor 42 of the amplifier 39. A fine adjustment variable resistor 43 is connected between the center contacts 35,36 of the switch 32. The lower right contact 38 is connected through a resistor 44 to the emitter of the transistor 42. The upper right contact 34 is connected to the center contact of a single pole double throw switch 46. A range resistor 47 is connected between the upper and lower contacts of the switch 46; and a coarse adjustment variable resistor 48 is connected between the upper contact of the switch 46 and the emitter of the transistor 42.

A double pole double throw switch 49, having upper and lower right contacts 51,52, center contacts 53,54, and left contacts 56,57, is connected from the lower center contact 54 to the grounded conductor 27. The center contacts 53,54 are connected, and the upper right and lower left contacts 51,57 are connected to the emitter of the transistor 42, to one side of a normally open battery test switch 58, and to a light emitting diode 59. The diode 59 is connected through a resistor 61 to conductor 26. The test switch 58 through a resistor 62 and the collector of the transistor 42 are connected to one side of meter 63 and to a terminal 64 connected to a strip-chart recorder (not shown). The other side of meter 63 connects through a resistor 66 to a switch 67 normally closed on terminal 68. When the switch 67 is not closed on terminal 68, circuitry (not shown) connects the recorder (not shown) to the terminal 68.

A feedback oscillator 69 includes a second amplifier 71 and a feedback circuit 72. The amplifier 69 includes a PNP transistor 73 connected at its base to terminal 68, at its emitter to conductor 26 and at its collector to the base of NPN transistor 74. The emitter of transistor 74 is connected to the lower right contact 52 of switch 49. The feedback circuit 72 includes a resistor 76 and capacitor 77 connected in series between the collector of transistor 74 and the base of transistor 73. A speaker 78 for producing an audio signal is connected between the collector of transistor 74 and conductor 26.

When, as in FIG. 3, a doctor 79 is to undertake diagnostic scanning of the body of a patient 81, an electrode 82 is grasped by the patient 81. The electrode 82 is connected to the second input 29. The circuit (FIG. 2) is actuated by the switch 49, and a D.C. potential is applied between the electrode 82 and either the single probe 11, the conducting member 17 being connected to first input 28, or a plate (not shown) connected to the input 28.

The doctor 79 then places the tapered end 18 of the probe 11 against the back of the patient 81 or grasps the plate (not shown) or second electrode (not shown) in one hand and touches the back of the patient with his free hand, as is illustrated in FIG. 3, thereby completing a circuit. The hand of the doctor 79 or the probe 11 is passed over the back of the patient 81 to detect areas along the spine meriting closer examination and treatment. The first pass down the back of the patient is along line 83 over the spinous processes, and second passes are made along lines 84 over the transverse processes. If further passes are made or if acupuncture points are being located, the hand of the doctor 79 or the probe 11 is moved to areas not along lines 83,84. The technique of palpation may be used also simultaneously.

Changes in resistance between inputs 28,29, and therefore in the body areas of the patient 81, are detected by the circuit shown in FIG. 2. Changes in resistance of the thermistor 21 of the probe 11, between inputs 30,31, and therefore changes in the temperature of the body areas of the patient 81, are also detected. The circuit (FIG. 2) indicates and feeds back to the doctor the temperature and resistance changes through either the meter 63, the strip chart recorder (not shown) or an audible signal from the speaker 78. The changes in temperature and resistance indicate to the doctor acupuncture points or areas along the spine which should be more closely examined and treated. The apertures 19 prevent the main portion of the conducting member 17 from becoming a large heat sink, thereby heightening the response of the tapered end 18, and therefore also of the thermistor 21, to temperarture changes.

If the double probe 12 is used, a circuit shown in FIG. 2 is provided for each of the individual members of the probe 12. The double probe 12 can be passed over the transverse processes along lines 84 on both sides of the line 83 of spinous processes simultaneously to give comparative readings.

The circuit in FIG. 2 is actuated by throwing the switch 49 such that contacts 53 and 51 are connected and contacts 54 and 52 are connected, if the meter 63 and speaker 78 are to be used, or by throwing the switch 49 to connect contact 53 with contact 56 and contact 54 with contact 57, if only the meter 63 is to be used. The light emitting diode 59 indicates when the circuit is on, and the switch 67 is used to connect the recorder (not shown) with the circuit.

The circuit senses the resistance changes of the body areas between inputs 28,29 when the switch 32 is thrown to connect contacts 33 with 35 and 34 with 36. The circuit senses the resistance changes of the thermistor 21, corresponding to temperature changes of the body areas, between inputs 30,31 when the switch 32 is thrown to connect contacts 35 with 37 and 36 with 38. A D.C. signal, corresponding to whichever resistance change is being detected, is input to and amplified by the first amplifier 39. The resistors 43, 48 adjust the amplifier 39, the pole of the switch 46 being thrown against the upper contact for normal range and against the bottom contact for extended range when necessary.

The amplified signal is indicated by the meter 63 or the recorder (not shown). The feedback oscillator 69 coupled to the speaker 78 converts the signal to an audible one variable in pitch.

The method disclosed herein is most effectively practiced when the hand of the doctor 79 or the probe 11 or 12 is passed over the back of the patient 81 at a constant pressure. Electrodes connected to inputs 28,29 and contacting the skin adjacent each other in an area such as the palm of the hand of the patient 81 are used when galvanic skin response is measured. Thus it can be seen that the objects of this invention are attained.

Although a preferred embodiment of a probe 11, a preferred method and modifications thereof have been disclosed herein, it is to be remembered that various modifications and alternate constructions can be made thereto without departing from the full scope of the invention, as defined in the appended claims.

I claim:

1. A method of aiding diagnostic scanning of the back of a patient by a doctor which comprises:
   disposing a first electrode held in the hand of the patient;
   disposing a probe means held in the hand of the doctor, said probe means including a resistance detecting means and a temperature detecting means, said temperature detecting means includng a resistive means for responding to temperature changes;
   applying a D.C. voltage to said electrode and to said resistance detecting means to cause a potential difference therebetween;
   placing said probe means against the body of the patient to complete a circuit, said circuit including said electrode, said resistance detecting means, said temperature detecting means, and said D.C. voltage source connected between said electrode and said resistance detecting means, said circuit further including means for responding to changes in resistance connected to said electrode, said resistance detecting means, and said temperature detecting means of said probe means, said circuit including means for indicating resistance and temperature responses coupled to said responding means, said resistance detecting means and said temperature detecting means being simultaneously pressed against the body of the patient;
   scanning the body of the patient by passing said probe means over the body of the patient;
   measuring the resistivity of the area of the patient's body pressed against by said probe means by detecting changes in the resistance between said resistance detecting means and said electrode;
   simultaneously measuring the temperature of the area of the patient's body pressed against by said probe means by detecting changes in the resistance of said resistive means;
   feeding back to the doctor the responses of said circuit to resistance changes indicating the resistivity and the temperature of the area of the body being pressed against by said probe means, whereby areas of the body of the patient to be closely examined and treated are more thoroughly located.

2. A method of aiding diagnostic scanning as described in claim 1 and further wherein a pair of said probe means are joined together in a transversely spaced manner, and scanning the body of the patient includes simultaneously passing said pair of probe means over the transverse processes on each side of the spinous processes of the spine of the patient.

3. A probe apparatus for use with a circuit for detecting and indicating changes in resistance in aiding diagnostic scanning of the back of a patient comprising:
   an external elongated insulating member; and
   an internal elongated conducting means for simultaneously conducting a current and heat from a body area against which it is pressed so that the resistivity and the temperature of the body area are simultaneously detected, said conducting means being within said external insulating member and projecting at one end therefrom, said conducting means including temperature detecting means and resistance detecting means, a first conductor means for connecting said resistance detecting means and said temperature detecting means to the circuit, a second conductor means for connecting said temperature detecting means to the circuit, said resistance detecting means having a conductive tapered end at said conducting means projecting end, said tapered end having a slightly curved tip portion, said temperature detecting means having a resistive means for responding to changes in temperature by transmitting a variable amount of current, said resistive means being formed in and encircled by said tip portion, said tapered end conducting a current from an area of the body of a patient through said tip portion adjacent to said resistive means and conducting heat from the body area and said resistive means responding to heat from the body area and from said tapered end when said tapered end is pressed against the body area, whereby changes in the resistance and the temperature of the body area are detected simultaneously.

4. A probe apparatus as defined in claim 3 and further wherein a plurality of apertures are formed about the periphery of said internal member adjacent said tapered end, and narrow portions formed between said apertures join said tapered end to said internal member, whereby responsiveness of said tapered end to heat changes of the body area is increased.

5. A probe apparatus as defined in claim 4 and further wherein a plurality of parallel external members are joined and transversely spaced, each of said external members having an internal conducting means affixed thereto, said tapered ends of said conducting means being extended in the same direction, said external members being spaced apart such that the distance between said tip portions of said tapered ends is that distance between the lines of the transverse processes of the patient.

* * * * *